United States Patent
Cameron et al.

(10) Patent No.: US 9,999,482 B2
(45) Date of Patent: Jun. 19, 2018

(54) ARCHWIRE ASSEMBLY WITH NON-LINEAR CRIMPABLE ORTHODONTIC STOP AND METHOD OF MANUFACTURE

(71) Applicant: Ultimate Wireforms, Inc., Bristol, CT (US)

(72) Inventors: Thomas B. Cameron, Avon, CT (US); William Joseph Porciello, Jr., Bristol, CT (US); Brian J. Case, Terryville, CT (US)

(73) Assignee: Ultimate Wireforms, Inc., Bristol, CT (US)

( * ) Notice: Subject to any disclaimer, the term of this patent is extended or adjusted under 35 U.S.C. 154(b) by 223 days.

(21) Appl. No.: 14/803,373

(22) Filed: Jul. 20, 2015

(65) Prior Publication Data
US 2016/0015481 A1    Jan. 21, 2016

Related U.S. Application Data

(63) Continuation of application No. 13/800,788, filed on Mar. 13, 2013, now Pat. No. 9,084,652.

(51) Int. Cl.
| | |
|---|---|
| *A61C 3/00* | (2006.01) |
| *A61C 7/20* | (2006.01) |
| *A61C 7/22* | (2006.01) |
| *A61C 7/28* | (2006.01) |
| *B23P 11/00* | (2006.01) |

(52) U.S. Cl.
CPC ............... *A61C 7/20* (2013.01); *A61C 7/22* (2013.01); *A61C 7/28* (2013.01); *B23P 11/005* (2013.01); *Y10T 29/49568* (2015.01)

(58) Field of Classification Search
CPC .... A61C 7/22; A61C 7/28; A61C 7/20; B23P 11/005; Y10T 29/49568
USPC ........... 408/8–22; 439/442, 421, 585, 607.5, 439/730, 741, 877, 878; 174/84 C, 94 R, 174/93
See application file for complete search history.

(56) References Cited

U.S. PATENT DOCUMENTS

| | | | |
|---|---|---|---|
| 1,998,518 | A | 4/1935 | Mraz |
| 3,614,716 | A | 10/1971 | Jensik |

(Continued)

OTHER PUBLICATIONS

International Search Report and Written Opinion dated Jul. 1, 2014 (PCT/US2014/020622).

*Primary Examiner* — Yogesh Patel
(74) *Attorney, Agent, or Firm* — Alix, Yale & Ristas, LLP

(57) ABSTRACT

An archwire stop defines a non-linear path through the stop that results in a bend moment between an orthodontic stop and the portion of an orthodontic archwire passing through the stop. The bend moment is accommodated by elastic deformation of the archwire and stop, resulting in a predictable frictional engagement between the stop and the archwire that is useful in maintaining a stop mounted on an archwire during packaging, shipping and handling in a clinical setting. A non-linear path through an archwire stop may be created by a non-linear tubular stop or may be created by appropriate internal features of the stop. The non-linear path through the stop may be selected so that the frictional engagement is greatest toward the free ends of the archwire, preventing the stop from sliding off the ends of an archwire, while permitting adjustment of the stop at the front of the mouth during patient treatment.

10 Claims, 6 Drawing Sheets

(56) References Cited

U.S. PATENT DOCUMENTS

| | | |
|---|---|---|
| 4,202,100 A | 5/1980 | Forster |
| 5,306,142 A | 4/1994 | Richards |
| 5,380,197 A | 1/1995 | Hanson |
| 5,910,008 A | 6/1999 | Tran |
| 6,213,649 B1 | 4/2001 | Omiya et al. |
| 7,160,106 B2 | 1/2007 | Farzin-Nia et al. |
| 7,314,317 B2 | 1/2008 | Hamasaki et al. |
| 8,672,676 B2 | 3/2014 | Farzin-Nia et al. |
| 2005/0191592 A1* | 9/2005 | Farzin-Nia ............... A61C 7/00 433/22 |
| 2006/0017282 A1* | 1/2006 | Claus .................... F16L 13/141 285/179 |
| 2007/0042314 A1 | 2/2007 | Brosius |
| 2007/0087301 A1 | 4/2007 | Farzin-Nia et al. |
| 2007/0269764 A1 | 11/2007 | Feller |
| 2008/0131831 A1 | 6/2008 | Abels et al. |
| 2009/0186313 A1 | 7/2009 | Chen et al. |
| 2010/0323316 A1 | 12/2010 | Taylor |
| 2012/0053687 A1* | 3/2012 | Migliazza ............. A61F 2/2448 623/2.37 |
| 2012/0107760 A1 | 5/2012 | Eichenberg |
| 2014/0302448 A1* | 10/2014 | Cassalia .................. A61C 7/28 433/9 |

* cited by examiner

ARCHWIRE ASSEMBLY WITH NON-LINEAR CRIMPABLE ORTHODONTIC STOP AND METHOD OF MANUFACTURE

BACKGROUND

The present disclosure relates to stops commonly used on orthodontic archwires in combination with tooth-mounted orthodontic brackets for treatment of tooth alignment issues. More particularly, the present disclosure relates to stops that define a non-linear path for an archwire to minimize sliding on the archwire, archwire assemblies incorporating such stops pre threaded on the archwire and methods of manufacturing archwire assemblies incorporating such stops.

Orthodontic treatment normally involves the application of mechanical forces to urge improperly positioned teeth into correct alignment. One common form of orthodontic treatment includes the use of orthodontic brackets that are fixed to teeth commonly by adhesively bonding the brackets directly to the teeth. A resilient curved archwire is then seated in the archwire slots of the brackets to impart mechanical forces to the teeth via the bracket. In traditional orthodontic treatment, the archwires may be secured to the brackets by ligature wires or elastic bands, which can limit relative movement between the archwire and the brackets. It has been found that free movement of the archwire relative to orthodontic brackets facilitates tooth movement, which is a goal of orthodontic treatment. Brackets of the self-ligating type were developed to eliminate the need for wires or elastic ligatures in securing archwires to orthodontic brackets and permit greater freedom of relative movement between the archwire and the brackets.

Brackets of the self-ligating type include a movable cover that selectively closes the archwire slot of the brackets to secure the archwire to the bracket, eliminating the need for ligature wires or elastic bands. The movable cover is opened for inserting the archwire and then closed for retaining the archwire within the archwire slot. The archwire is elastically deformed to engage the brackets, and seeks to return to its designed curve, thereby imparting mechanical force that urges the teeth to move to the correct position over time. Once secured in the archwire slot by the cover, the archwire is free to move laterally in the archwire slot, which facilitates tooth movement during treatment.

The enhanced freedom of movement of the archwire relative to self-ligating brackets can result in undesirable migration of the archwire from its intended installed position. Unbalanced forces produced by the tongue, mouth muscles and chewing will move the archwire laterally through the archwire slots of the brackets. This movement may cause a free end of the archwire to protrude from one of the brackets attached to the molars and contact gum or cheek tissue. As a result of the movement, the opposite free end of the archwire may also become disengaged from its bracket. The protruding ends of the archwire can irritate the gum or cheek tissue. Further, orthodontic treatment is disrupted by release of the archwires from the brackets.

Several conventional techniques are used to limit movement of the archwire in the bracket slots to prevent disengagement of the archwire from the brackets as well as to direct forces to one or more teeth. One technique is to insert the archwire through a crimpable sleeve, such as a small diameter tube, then position the archwire within the bracket slots with the sleeve located between two adjacent brackets. The sleeve is then secured (crimped) to the archwire at a fixed position to form a stop. The sleeve is configured such that the sleeve cannot pass through or move beyond an archwire slot as the archwire moves in the lateral direction. In this manner, the maximum movement of archwire is limited to somewhat less than the distance between the adjacent brackets. This arrangement effectively prevents the free ends of the archwire from becoming disengaged from the molars at the back of the mouth while permitting free movement of the archwire relative to the bracket.

There are inherent complications with the use of stops in the clinical setting. The principle problem is their very small size. Typical stops are about 10 to 30% of the size of an orthodontic bracket. Tubes used for stops are often 0.03" to 0.04" in diameter and only 0.08" long. Tubes are mounted on the archwire in clinical settings such as a doctor's office, usually by the dentist or a dental assistant. It can be a challenge to see and handle these very small components, which then tend to slide freely along the archwire under their own weight. These small tubes may either slide to the wrong location for treatment or slide off the wire completely after being threaded onto the archwire but prior to installation being completed. A similar complication occurs when the clinician uses multiple stops on a single wire and must control the stop location as the archwire is being placed in the patient's mouth. FIG. 2 illustrates a prior art stop mounted on an archwire, where the stop is free to slide along the archwire as described above.

It is known to provide assemblies with tubes (stops) that are pre-mounted on archwires. One common method is to deform (partially crimp) the stops against the archwire (also termed 'flattening') so as to limit the sliding motion and thereby prevent the stop from falling off of the archwire. Since archwires are typically curved in a flat plane, is intuitive to flatten the stop in a direction that is 90 degrees to the plane P of the archwire as shown in FIG. 3. The flattening method attempts to generate a sliding friction between the wire and stop by pressing the tube hard against the wire to create local wire-to-stop contact pressure across the width of the wire as shown in FIG. 4.

For the flattening process to work in a clinically acceptable manner, it is important to maintain a controlled amount of friction between the stop and the wire. Friction is generated by the clamping pressure of the flattened stop across the diameter of the wire as shown in FIG. 4. Though stop flattening is a simple concept, manufacturing experiments have shown that the typical small variations in the dimensions of the wires and stops result in large variations in the friction of the stops on the wires. Large variations in friction result in some stops that either fall off of the archwire or are too tight and cannot be moved easily by the clinician. Other methods of deforming the stops such as notching and pre-crimping (localized indentations as shown in FIG. 5), or partial crimping utilize the same general phenomena (pressure against the width of the wire) to produce local tube-to-wire friction at the site of the notch or crimp and hence are subject to the same unacceptably large variation in friction.

Another shortcoming of the flattening stop approach is that the friction between the stop and wire changes as the stop is moved along the wire. This occurs because the sliding friction is generated by small contact areas between the stop and wire and these small contacts wear off quickly with a small amount of sliding. A stop with adequate initial friction may lose that friction with clinical sliding adjustments. Increases in sliding friction have also been observed, which can be caused by slight increases in wire dimensions (because wire dimensions can change locally within their tolerance range during production processes). Also the stops themselves are often a soft metal and galling (soft metal smearing) can increase friction quickly. Fundamentally, these problems result from the reliance on contact pressure between stop and wire that is directed across the thickness dimensions of the wire. This contact pressure (and resulting friction) changes dramatically with small changes in dimensions in their zones of contact whether due to local wear or wire dimension changes.

There is a need for an improved archwire assembly that eliminates the need for field assembly of stops onto an archwire. An additional need is that a tube placed on the archwire will predictably remain in place during packaging, shipping and installation, but is easily moved to a desired position for final crimping.

SUMMARY OF THE DISCLOSURE

An archwire stop defines a non-linear path through the stop that results in frictional engagement between the archwire and the stop. The non-linear path through the stop is designed to create contact between the archwire and the stop to impose a bend on the archwire as it passes through the stop. The term "bend" as used in this application is synonymous with "bend moment" and describes a situation of unbalanced contact between the stop and archwire. Depending upon the structural properties of the archwire and corresponding stop, the stress of the resulting bend may be absorbed by reversible deformation (bending) of the archwire, the stop, or a combination of both. The dimensions and properties of the stop and archwire may result in bending forces that are difficult to measure, but are evident in the variable frictional engagement between the stop and archwire at differently curved portions of the archwire as described in greater detail below.

The bending force is resisted by the elastic nature of the archwire and stop and results in a predictable frictional engagement between the stop and the archwire that is useful in maintaining a stop mounted on an archwire during packaging, shipping and handling in a clinical setting. A non-linear path through an archwire stop may be created by a non-linear tubular stop or may be created by appropriate internal features of the stop. The non-linear path through the stop may be selected so that the frictional engagement is greatest toward the free ends of the archwire, preventing the stop from sliding off the ends of an archwire. In some embodiments, frictional engagement is least toward the center (anterior) of the archwire where the curvature of the archwire most closely matches the bend imparted by the stop, making repositioning the stop straightforward during orthodontic treatment in a clinical setting. A variety of non-linear stop configurations will impart the desired bend in an archwire and include curved, bent, dimpled, symmetrical and asymmetrical configurations.

There are several types of archwires used in orthodontic treatment. Common archwire materials include NiTi (Nickel Titanium), stainless steel and non-nickel containing wire material such as beta titanium. NiTi alloys may include between 1 to 10% Cu, Co, Nb, Pd or combinations thereof. Nickel free Beta Titanium wires may include primary elements of Ti, Mo, Zr and 0-5% of additional elements selected from Sn, Al, Cr, V, and Nb or combinations thereof. Archwires are typically solid metal with cross sections that are round, square or rectangular. Other types of wires are also used and these can include stranded and braided metal wires as well as newer polymer, plastic, ceramic and combinations of these materials. Nonmetallic materials may be combined with metallic materials to produce a composite archwire. Archwires constructed of these materials are designed to impart pre-determined mechanical forces on the brackets (and the associated teeth) through which they pass. Archwire materials exhibit significant elastic properties, permitting them to be deformed to pass through misaligned tooth-mounted orthodontic brackets and return to their pre-deformation shape, moving teeth in the process. As used in this application, the word "archwire" is intended to encompass orthodontic archwires without regard to the material from which the archwires are constructed or their sectional configuration, whether solid, stranded, round, rectangular or square. Archwire, as used in this application is expressly not limited to orthodontic archwires constructed of metallic wire materials.

Archwire stops are made in shapes compatible with the various archwires and so are produced in circular, square, and rectangular cross sectional shapes. Stops may be constructed of seamless tubing, welded tubing, split tubing, or slotted tubing, e.g., tubing that is discontinuous in its circumference. Tubular stops are typically fabricated from wrought ductile metal. Ductility is needed for the flattening, notching or crimping deformation that is required to produce the wire-stop friction. Soft stainless steel is often used to construct orthodontic stops. As the tube material is typically softer than the metal wire, the process of deforming the tube is not expected to damage most metal wires. However, the flattening, crimping and notching processes for metal tubes are not expected to be compatible with non-metal wires. Orthodontic stops may include continuous round shapes, square shapes, rectangular shapes, more complex or random cross sectional shapes. Orthodontic stops may be constructed of other, non-metallic materials or metallic materials coated to resemble tooth color for aesthetic reasons. The word "stop" as used in this application is defined to encompass an orthodontic stop without regard to material or sectional configuration. The words "tubes" and "sleeves" are used interchangeably and are both forms of an orthodontic "stop".

Disclosed methods of manufacture include using a pair of dies to deform one or more stops while the stops are mounted on an archwire. The archwire supports the stop during forming to limit changes to the tubular cross section of the stop. The relatively elastic archwire is not deformed, but the stop is deformed to a non-linear configuration which "grips" the archwire by forcing the archwire to bend slightly as it passes through the stop. The non-linear shape of the stop may be selected to impart a pre-determined frictional engagement between the stop and the archwire.

DETAILED DESCRIPTION OF THE DISCLOSED EMBODIMENTS

Figure 1:
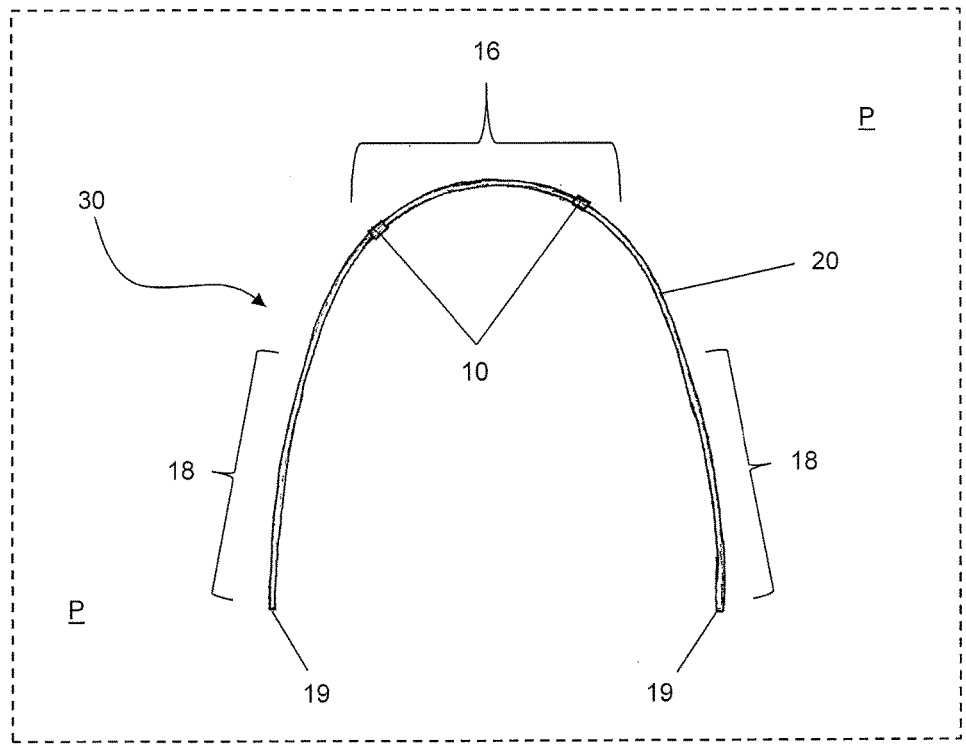
FIG. 1 shows an archwire with two stops assembled on the archwire to form an archwire assembly.
Figure 2:
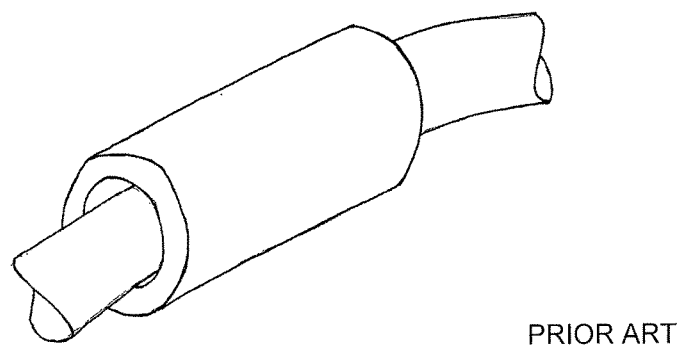
FIG. 2 is an illustration of a common straight tubular stop on an orthodontic wire.
Figure 6:
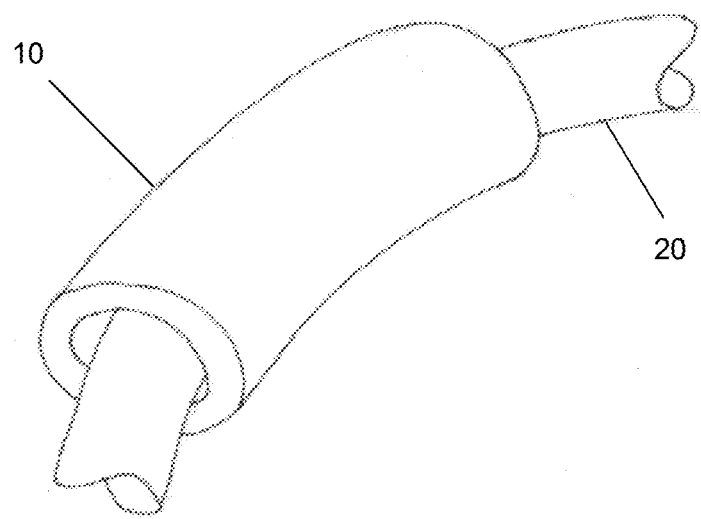
FIG. 6 is an illustration of a non-linear tubular stop on an archwire according to aspects of the present disclosure.
Figure 7:
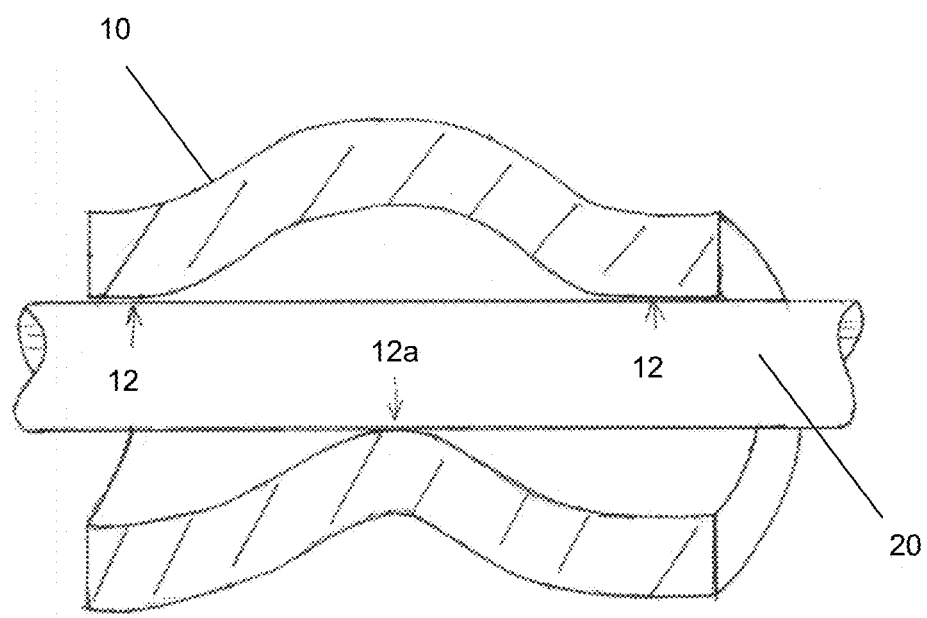
FIG. 7 is a cross section of an archwire assembly incorporating a non-linear tubular stop illustrating the 3-point contact pattern that generates a bending force on the archwire within the stop.
Figure 10:
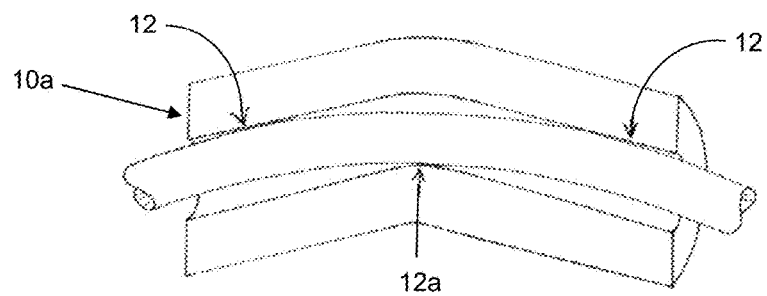
FIGS. 10 and 11 are schematic views of alternative non-linear stop configurations according to aspects of the present disclosure.
Figure 11:
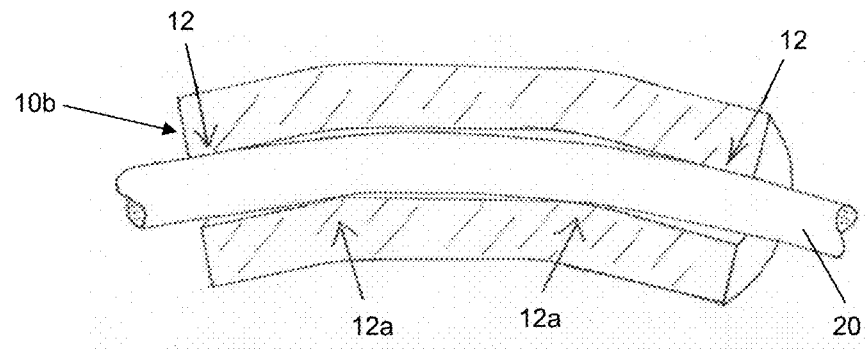
Figure 12:
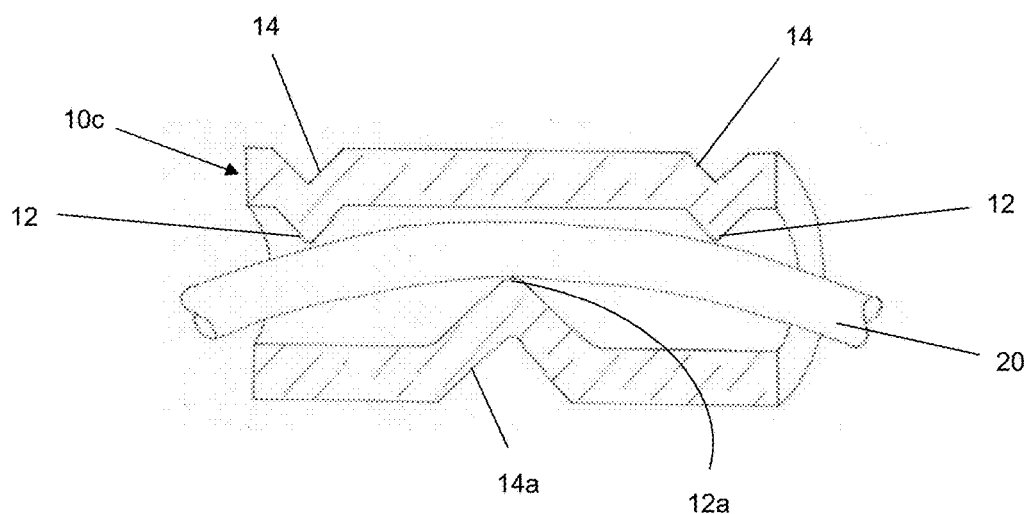
FIG. 12 is a schematic representation of a linear stop that defines a non-linear path for the archwire passing through the stop.

Several embodiments of a non-linear configuration for crimpable orthodontic stops are disclosed. The term "non-linear" as used in this application means "not straight" and is intended to encompass any stop configuration which imparts a bend (bending moment) to the archwire passing through the stop. Points of contact 12 on the inside surface of a stop 10 force an archwire 20 to bend when passing through the stop. Suitable features on the inside surface of a non-linear stop 10 may be created without bending the entire stop, but may result from a particular pattern of projections 14 toward a central axis of the stop 10c as shown in FIG. 12. An alternative approach is to bend all or part of the stop into a non-linear configuration, such as a curve of a suitable radius. Non-linear configurations specifically contemplated as falling within the meaning of this term are illustrated in FIGS. 6, 7, and 10-12. A first embodiment is a design that uses lengthwise curvature in a tube to produce reliable control of sliding friction on an archwire. As shown in FIGS. 6 and 7, a non-linear stop 10 is mounted on an archwire 20. One or more non-linear stops 10 may be assembled on an archwire to produce an archwire assembly 30 as shown in FIG. 1.

Stop sectional dimensions are selected to prevent movement into the slot of an orthodontic bracket. For this reason, the tube dimensions are intentionally larger than bracket slots they are used with. For example, a common orthodontic bracket slot width nominal dimensions are 0.018" and 0.022" and stop outside diameter (O.D.) values for use with a particular bracket will be larger than these slot dimensions, as discussed in greater detail below. Stops 10 are constructed from tubular materials defining a central passage chosen to slide on an archwire 20. As a result, the nominal inside diameter (or minor dimension for other shapes) will be somewhat larger than the diameter of archwires 20 with which the stops 10 will be used.

Non-linear stops create friction from the production of a bending moment between a length of the wire against at least a portion of the length of the tube (refer to FIGS. 7 and 10-12). The advantage of the bending moment is that it utilizes the inherent flexibility of the wire (and to a lesser extent, the stop) to generate a more predictable and repeatable sliding friction. The friction generated by a bending moment is significantly less influenced by variation in the stop and wire sectional dimensions and is therefore inherently more predictable. Friction between a non-linear stop and an archwire is also less likely to vary as a result of sliding the stop on the archwire during installation or adjustment.

An added advantage of non-linear stops is that the design eliminates the problem of tubes falling off the ends of the archwire. Archwires can be described as having a shape that is similar to an inverted "U" as shown in FIG. 1. The anterior (front) portion 16 of an archwire 20 has greater curvature than the posterior (rear) end portions 18. Another way to describe the curvature of the archwire 20 is that it is defined by a smaller radius of curvature at the front (anterior) of the mouth and a larger radius of curvature toward the free ends 19 of the archwire 20 which extend toward the molars at the rear (posterior) of the mouth. Archwire curvatures are not limited to circular curve portions based on one or more radii, and may include parabolic, elliptical and/or aspheric curved portions. Curvature descriptions that reference a radius of curvature are a convenient way of discussing the difference between the designed curvature of an archwire and the curvature of the archwire resulting from the bend moment imposed on the archwire as it passes through a non-linear stop. In the disclosed embodiments, the non-linear path defined by the disclosed stops 10, 10a, 10b, 10c is selected to impart a bend having a radius of curvature less than the largest radius of curvature on the archwire. This configuration ensures that, at the posterior regions (legs) 18 of the archwire having the largest radius of curvature, the stop 10, 10a, 10b, 10c is configured to grip the archwire 20 and not slide off. An alternative disclosed stop may be configured to impart a bend having a radius of curvature less than the smallest radius of curvature on the archwire 20 to ensure at least some frictional engagement between the stop 10 and archwire 20 even at the front of the archwire (anterior portion 16), where the radius of curvature is typically the smallest.

It is important to note that while most orthodontic archwires are curved in a flat plane P as shown in FIG. 1, other archwires have curvature in two perpendicular planes. Such compound curved archwires are compatible with the disclosed non-linear stops and are intended to be encompassed by the term "archwire" as used in this application and the appended claims.

With the desired attributes of a non-linear path through the stop in mind, it is possible to calculate the dimensions and interior features of a stop that will impart a bend moment on the archwire 20 as it passes through the stop 10. Relevant variables are: the material, diameter, sectional shape and curvature of the archwire 20 as well as the inside diameter and length of the stop 10. For any given set of variables, there will be a minimum non-linearity required to ensure the stop 10 imparts a bend moment to the archwire 20 as it passes through the stop 10. Of particular relevance is the curvature of the archwire at the posterior (rear) portions 18, which may be referred to as "legs." An objective of the non-linear path-induced bend moment is to ensure the stop 10, 10a, 10b, 10c does not fall off the posterior free ends 19 of the archwire 20. This requires a minimum frictional engagement between the archwire 20 and the stop 10, 10a, 10b, 10c at least at the posterior portions 18 of the archwire.

One benefit of certain embodiments of the disclosed non-linear stops 10 is that the frictional engagement with the archwire 20 increases as the curvature of the archwire decreases. This variable frictional engagement is most likely when the non-linearity of the stop occurs in the same direction of curvature as the associated archwire 20. Stated another way, as the difference between the radius of curvature of the archwire 20 (in a free state) and the radius of bend imparted by the stop 10 increases, so does the frictional engagement between the stop 10 and the archwire 20. This results in increased frictional engagement between the stop 10 and archwire 20 at the relatively straight rear (posterior) portions 18 (legs) of the archwire 20 and reduced frictional engagement on the anterior portion 16 of the archwire toward the front of the mouth, where repositioning of the stop 10 on the archwire 20 is desirable. Stops having the disclosed non-linear configuration are prevented from falling off the ends 19 of the archwire 20 and remain moveable where needed by the practitioner. This design greatly minimizes the possibility of accidental loss of stops 10 from the posterior portion (rear leg 18/free ends 19) during handling and patient treatment.

Figure 3:
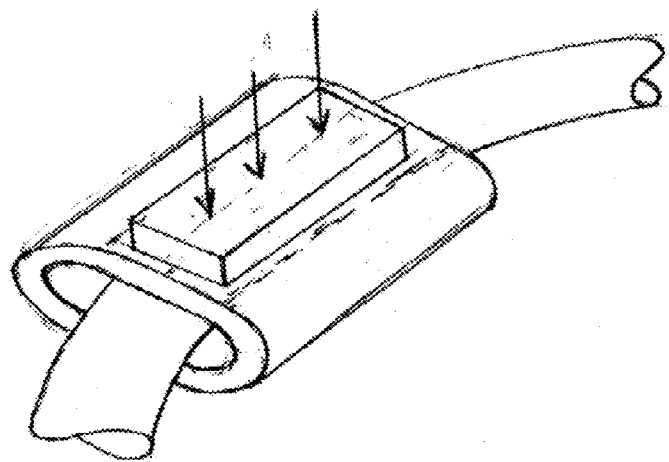
FIG. 3 illustrates a common prior art method of flattening a tubular stop on an archwire.
Figure 4:
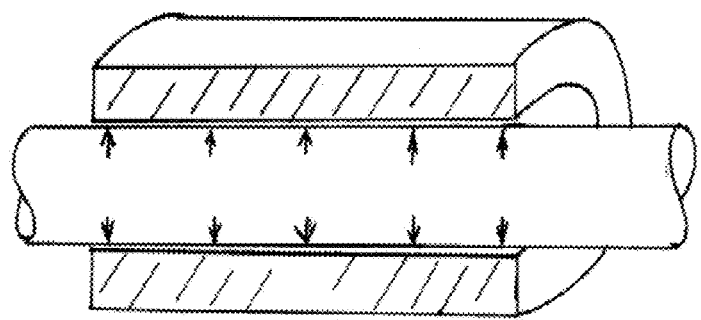
FIG. 4 is a cross section of a prior art flattened tubular stop illustrating the tube forces generating diametrical pressure on the archwire.
Figure 5:
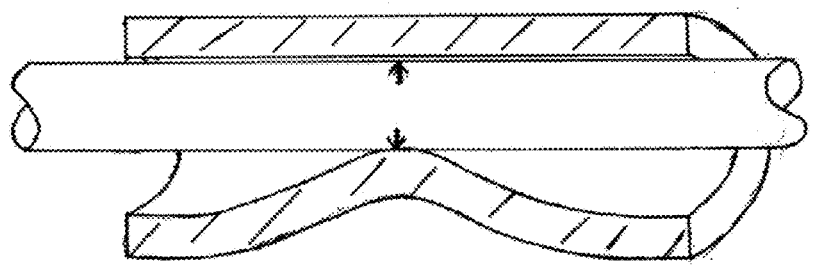
FIG. 5 is a cross section of a prior art dimpled tubular stop illustrating the forces generated by the dimpled stop on the archwire.

By contrast to the prior art flattened stop or partially crimped methods that produce frictional engagement at diametrically opposed points on an archwire (see FIGS. 3-5), the disclosed non-linear stops 10, 10a, 10b, 10c are intentionally designed to produce a length-wise bend moment between the archwire 20 and the stop 10, 10a, 10b, 10c as shown in FIGS. 7 and 10-12. The non-linear stop 10 results in contact with the archwire 20 at longitudinally separated points 12 on the archwire 20 to impart a bend moment in the archwire 20. The bending concept requires at least three points of contact 12 between the stop 10 and the archwire 20, with two of the points of contact 12 being separated by at least one intermediate point of contact 12a. The separated points of contact 12 will be on an opposite side of the archwire from the intermediate point or points 12a, but no points of contact will be diametrically opposed. As shown in FIGS. 7 and 10-12, points of contact 12 between the stop 10, 10a, 10b, 10c and archwire 20 are defined by the non-linear stop and are substantially fixed with respect to each other. The bending moment imposed by the stop 10, 10a, 10b, 10c is resisted by the elastic nature of the archwire 20, producing the predictable frictional engagement. From FIGS. 7 and 10-12, it is clear that the points of contact 12, 12a between the stop 10, 10a, 10b, 10c and archwire 20 are longitudinally separated and not diametrically opposed, as in the flattened or crimped tube approach show in FIGS. 4 and 5. This configuration reduces the influence of dimensional variation on the frictional engagement between the stop and the archwire. One significant difference between the prior art and the presently disclosed non-linear stops 10, 10a, 10b, 10c is illustrated by comparing FIGS. 4 and 5 (2-point contact/diametrically opposed) with FIGS. 7 and 10-12 (multi-point contact/longitudinally separated/not diametrically opposed).

Non-linear stops 10 according to the disclosure will produce a bend moment contact load condition when used with an appropriate archwire 20. A non-linear stop 10 according to the disclosure will have at least 3 substantially fixed points 12, 12a on the inside surface of the stop 10, 10a, 10b, 10c arranged to be simultaneously in contact with the archwire 20 with no 2 points of contact being diametrically opposed. Curved tube shapes that satisfy this requirement can be a simple lengthwise radius as shown in FIGS. 6 and 7 or a more complex shape containing compound radii or a tube with asymmetrical curve designs (not shown). FIGS. 10 and 11 illustrate non-linear stop configurations where the tubular stop 10a, 10b includes two or more straight segments arranged to provide the requisite points of contact 12, 12a and bending moment on the archwire 20. FIG. 10 illustrates a bent tubular stop 10a where two segments of equal length meet at an obtuse angle selected to produce the desired bend moment in the archwire 20. FIG. 11 illustrates a bent tubular stop 10b where three segments meet at two obtuse angles. The non-linear stop 10b of FIG. 11 has four points of contact with the archwire, two on the inside of the archwire 12a and two on the outside of the archwire 12, with no two points of contact 12, 12a being diametrically opposed to each other. The non-linear stop shapes 10, 10a, 10b illustrated in FIGS. 7, 10 and 11 are symmetrical, but this is not required. A curved or segmented stop may be asymmetrical and still include the multiple points of contact 12, 12a necessary to induce a bend moment in the archwire 20 passing through the stop 10. A simple example would be the two segment stop of FIG. 10 where one segment is longer than the other. Curved shapes can be generated along the tube length (inside and outside diameters) or on just the inside diameter.

One aspect of the disclosed non-linear stop is that the opening in the interior passage defined by the stop, at any given point along the stop, exceeds the archwire cross sectional dimensions, while contact between the wire at a minimum of three points on the inside surface of the stop generate an intentional bending moment between the stop and archwire sufficient to induce frictional engagement between the stop 10 and the archwire 20. Note that it is intended that a bend moment imparted between the stop 10, 10a, 10b, 10c and the archwire 20 is sufficient to create adequate friction but because the contact length of the stop is very short and the loads are low, these very local forces are not expected to impart a bending force great enough to exceed the elastic range of the archwire, which would distort the archwire from its intended clinical shape.

Depending upon the dimensions of the archwire 20 and the corresponding stop 10, the bending moment may elastically deform the stop 10, the archwire 20 or both. Whichever component deforms in response to the bending moment, a predictable frictional engagement between the stop 10 and the archwire 20 is the result.

FIG. 12 illustrates an orthodontic stop defining a non-linear path through the stop 10c, while the stop 10c itself remains substantially linear. Dimples 14, 14a project into the interior of the stop 10c to define three points of contact 12, 12a the archwire 20 must pass on its way through the stop 10c. Two of the dimples 14 are on the same side of the stop 10c, while the third dimple 14a is located between the other two dimples 14 and on an opposite side of the stop 10c. The three protrusions 14, 14a into the interior of the stop 10c impose a bending moment on the archwire 20 as it passes through the stop 10c, generating a predictable frictional engagement between the stop 10c and the archwire 20.

Non-linear configurations suitable for one archwire size may not be suitable for a significantly different wire size. Differently configured archwires may require stops with a specific non-linearity to produce an appropriate amount of friction (one curved tube may not work on all wire sizes). For rectangular wires (cross section width is different from wire height) the orientation of the curved stop may change the amount of friction generated. In this case, the orientation of the stop will be important. Differently configured stops may be needed for wires with significantly different bending stiffness or surface finish properties (example, stainless steel vs. NiTi).

Stops are typically hollow, round ductile metal but other shapes are possible. These shapes include hollow cross sections that are circular, elliptical, square, rectangular, or have more complex or irregular geometries. Tubes for use as stops on orthodontic wires are commonly produced from a wrought, softened (annealed) stainless steel. But other tube production methods (casting for example) may be compatible with the disclosed non-linear stops. Materials other than metal are compatible with the disclosed non-linear stops, but permanent fixation by means other than crimping may be necessary (i.e. glue or heat bonding may work better with polymer tubes than crimping).

Figure 8:
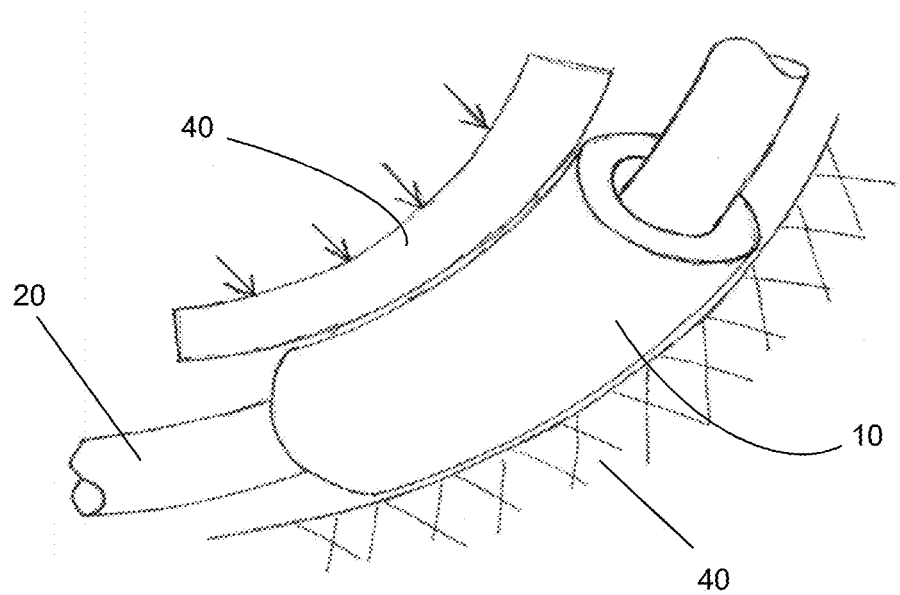
FIG. 8 is a perspective illustration of a method for forming a non-linear tubular stop and archwire assembly according to aspects of the disclosure.
Figure 9:
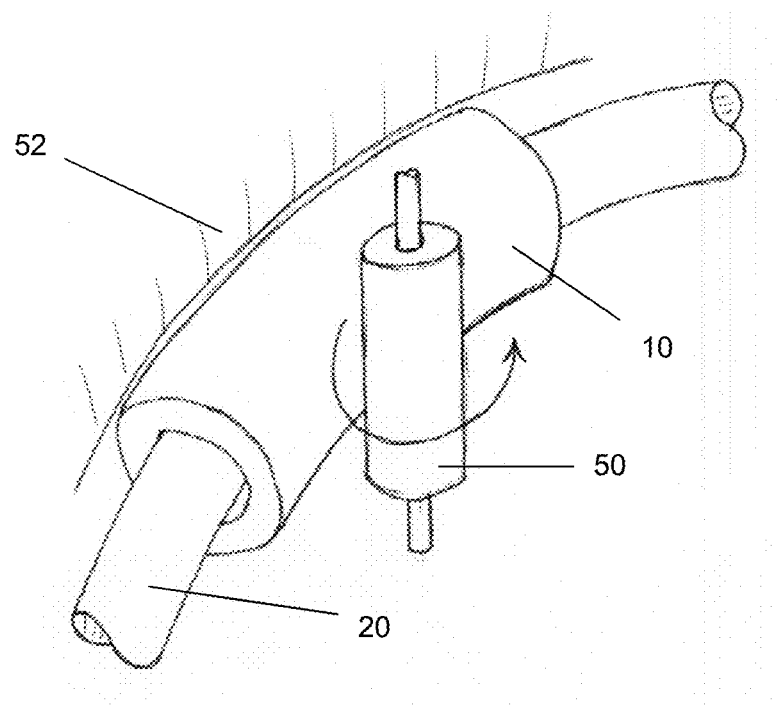
FIG. 9 is a perspective illustration of an alternative method for a non-linear tubular stop and archwire assembly according to aspects of the present disclosure.
Figure 13:
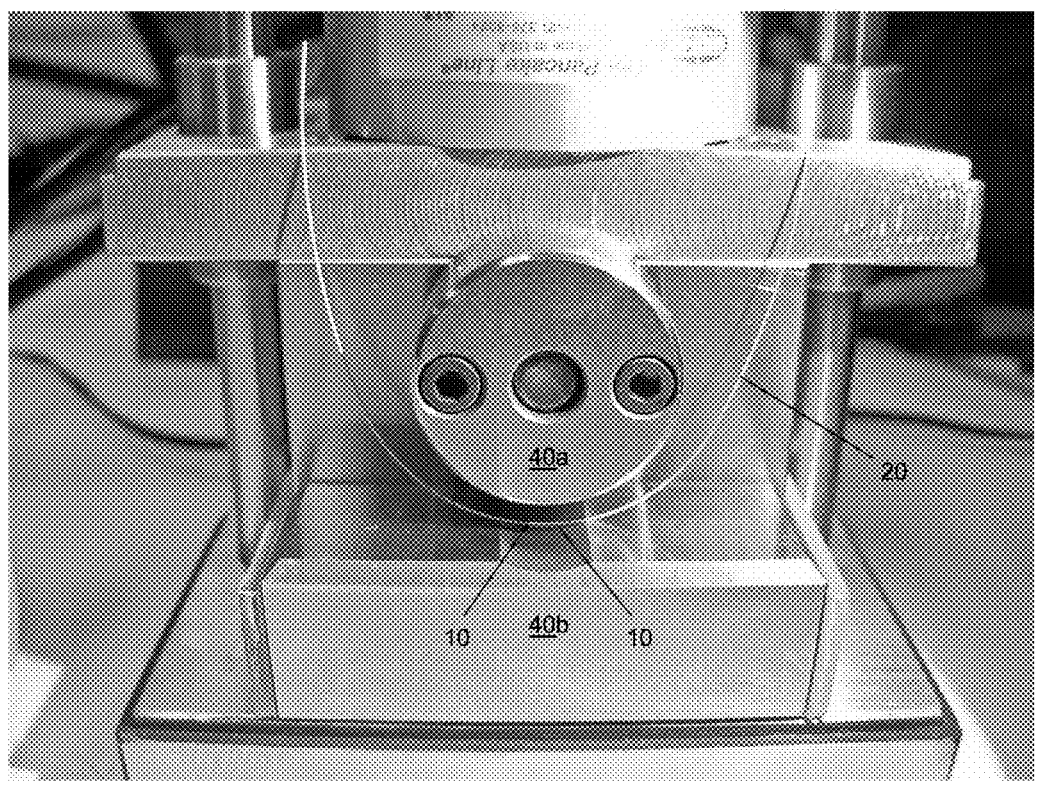
FIG. 13 shows an archwire with two stops assembled on it about to be exposed to dies that will impart a non-linear configuration to the stops.

Methods of manufacture will be discussed with reference to the curved non-linear stop 10 shown in FIG. 6. For purposes of discussion, the curve induced in a tubular stop may be described by reference to a single radius of curvature. A curve that is described by a radius implies a symmetrical bend or curve in the stop. The radius necessary to produce a suitable friction generating bend in the archwire will be a function of the wire size and curvature, tube I.D. size and tube length. There are several methods disclosed to produce a suitable curve or radius in a tube. One method is to press a selected tubular stop 10 having a pre-determined length and cross sectional dimensions between curved dies 40 as shown in FIGS. 8 and 13. This can be accomplished while the stop 10 is assembled on an archwire 20 or with the tubular stop independent of an archwire. The die pressing method of FIGS. 8 and 13 may be compatible with the non-linear stop configurations shown in FIGS. 10 and 11. A second disclosed method is to apply a rolling or forming element 50 to one side of the stop 10 with the opposite side of the stop 10 placed against a shaped die 52, a rigid substrate, a compliant substrate or another forming or rolling element as shown in FIG. 9. All of these combinations can be used to create a curve in a tube, and all can be used whether or not the tube is on a wire. Other methods of forming will occur to those skilled in the art and all such methods may be compatible with the disclosed non-linear stops.

However, as noted previously, a curvature that is not a symmetrical curve defined by a single radius may still function as intended for a non-linear stop according to the disclosure. Asymmetrical curves where the center of curvature is skewed toward one end or the other of the stop can provide the multipoint contact and bend moment as disclosed with respect to symmetrical non-linear stops. The disclosed methods of manufacture may be applied to generate non-linear configurations that are more complex than the simple non-linear configurations disclosed in FIGS. 7, 10 and 11.

Another approach to producing the disclosed non-linear stops is to manufacture tubing with suitable curvature utilizing commercial tube forming technologies. Individual tubes can be produced in this manner. Also, continuous or semi-continuous lengths having a desired non-linear configuration can be produced and cut to appropriate lengths.

Experimentation with fabrication of non-linear curved archwire stops reveals that the disclosed stops generate predictable and repeatable frictional engagement with an archwire. Experimentation has also proven that acceptable frictional engagement between a non-linear orthodontic stop and the most common sizes and shapes of archwires can be accomplished using only two sizes of stop material and two non-linear curved configurations as follows. "Small" stops are suitable for use with round wires 0.013", 0.014", 0.016", and 0.018" diameters. A small stop is 0.080" long, has an outside diameter (OD) of 0.032" and an inside diameter (ID) of 0.020". "Large" stops are suitable for use with 0.016", 0.018" and 0.020" square wires and 0.04"×0.025", 0.016"×0.022", 0.016"×0.025", 0.017"×0.025", 0.018"×0.025", and 0.019"×0.025" rectangular wires. Large stops are 0.080" long, have an OD of 0.042" and an ID of 0.032".

Matching die sets were prepared to form small and large stops while the stops are threaded on one of the associated archwires as shown in FIG. 13. Each die set includes a cylindrical male punch 40a and a matching female die block 40b having a concave cylindrical surface opposed to the male punch 40a as shown in FIG. 13. The die set for the small tubes includes a male punch with a forming surface radius measuring 0.710" and a female die block defining a surface having a radius of 0.750". The die set for large tubes includes a male punch with a forming surface measuring 0.960" in radius and a female die block defining a surface having a radius of 1.00". Two stops 10 were threaded onto an archwire 20 and placed between the male and female dies 40a, 40b as shown in FIG. 13. The dies 40a, 40b are then closed on the archwire assembly at predetermined pressures, which forms the stops 10 with a curvature that imparts a bending moment as the archwire passes through the stop. The resulting non-linear stops 10 were tested to see how much force was required to move the stop 10 relative to the archwire 20 at both the posterior (rear legs) 18 and anterior (front) portion 16 of the archwire 20.

Table 1 below shows the "minimum" die pressures that will form the stops and result in acceptable average sliding force at the posterior (rear) portions of the respective archwires. A frictional engagement that requires approximately 0.5 lbs. of force directed along the length of the archwire is sufficient to prevent the stop from sliding off the archwire during packaging, transport and patient care. So it is the left hand column, showing the minimum frictional engagement with the posterior portions of the archwire, which is of significance in the minimum pressure scenario. It will be seen that the sliding force required to move the stops on the anterior (front) portion of the archwires is consistently lower than the sliding force required to move the stop on the posterior (rear) portions of the archwire. Note the consistency of the frictional engagement of the formed non-linear stops at the anterior portion of the archwire as indicated by the standard deviation.

TABLE 1

Die Pressure Ranges for Assembly of Tubes on Archwires
Results from pressing values set at 'minimum' pressure

| | | | | | Posterior | | Anterior | |
|---|---|---|---|---|---|---|---|---|
| Wire Type | Wire Size Inches | Die Pressure (minimum) psi | Die Set | Tube Size | Average Tube Sliding Force, lbs | STDEV | Average Tube Sliding Force, lbs | STDEV |
| Round | 0.013 | 31 | Small | Small | 0.5 | 0.17 | 0.3 | 0.04 |
| | 0.014 | 31.0 | Small | Small | 1.0 | 0.33 | 0.4 | 0.13 |
| | 0.016 | 24.0 | Small | Small | 0.6 | 0.16 | 0.3 | 0.14 |
| | 0.018 | 22.0 | Small | Small | 0.6 | 0.22 | 0.2 | 0.02 |

TABLE 1-continued

Die Pressure Ranges for Assembly of Tubes on Archwires
Results from pressing values set at 'minimum' pressure

| | | | | | Posterior | | Anterior | |
| --- | --- | --- | --- | --- | --- | --- | --- | --- |
| Wire Type | Wire Size Inches | Die Pressure (minimum) psi | Die Set | Tube Size | Average Tube Sliding Force, lbs | STDEV | Average Tube Sliding Force, lbs | STDEV |
| Square | 0.016 × 0.016 | 25.0 | Large | Large | 0.3 | 0.10 | 0.2 | 0.05 |
| | 0.018 × 0.018 | 30.0 | Large | Large | 0.5 | 0.36 | 0.2 | 0.03 |
| | 0.020 × 0.020 | 41.0 | Large | Large | 0.4 | 0.25 | 0.1 | 0.03 |
| Rectangle | 0.014 × 0.025 | 41.0 | Large | Large | 0.5 | 0.19 | 0.2 | 0.01 |
| | 0.016 × 0.022 | 30.0 | Large | Large | 0.5 | 0.16 | 0.2 | 0.03 |
| | 0.016 × 0.025 | 40.0 | Large | Large | 0.7 | 0.36 | 0.2 | 0.09 |
| | 0.017 × 0.025 | 40.0 | Large | Large | 0.5 | 0.20 | 0.2 | 0.01 |
| | 0.018 × 0.025 | 40.0 | Large | Large | 0.7 | 0.21 | 0.2 | 0.02 |
| | 0.019 × 0.025 | 40.0 | Large | Large | 0.8 | 0.35 | 0.2 | 0.04 |
| | | | | Avg = | 0.5 | 0.24 | Avg = 0.2 | 0.05 |

Table 2 below shows experimental results for die pressures at values that produce maximum acceptable frictional engagement between the stop and the anterior (front) portion of the archwire as shown in the right hand column. This frictional engagement cannot be so great as to interfere with the clinical installation of the archwire assembly, which requires adjustment of the position of the stop along the archwire. Again, the frictional engagement with the anterior of the archwire is significantly less than the frictional engagement with the posterior of the archwire.

TABLE 2

Results from pressing values set at 'maximum' pressure

| | | | | | Posterior | | Anterior | |
| --- | --- | --- | --- | --- | --- | --- | --- | --- |
| Wire Type | Wire Size Inches | Die Pressure (maximum) psi | Die Set | Tube Size | Average Tube Sliding Force, lbs | STDEV | Average Tube Sliding Force, lbs | STDEV |
| Round | 0.013 | 35.0 | Small | Small | 0.8 | 0.22 | 0.5 | 0.2 |
| | 0.014 | 35.0 | Small | Small | 1.1 | 0.43 | 0.7 | 0.4 |
| | 0.016 | 30.0 | Small | Small | 1.7 | 0.74 | 1.0 | 0.5 |
| | 0.018 | 30.0 | Small | Small | 1.6 | 0.48 | 0.4 | 0.1 |
| Square | 0.016 × 0.016 | 70.0 | Large | Large | 0.6 | 0.14 | 0.2 | 0.0 |
| | 0.018 × 0.018 | 70.0 | Large | Large | 0.8 | 0.41 | 0.2 | 0.0 |
| | 0.020 × 0.020 | 70.0 | Large | Large | 0.6 | 0.18 | 0.0 | 0.0 |
| Rectangle | 0.014 × 0.025 | 70.0 | Large | Large | 1.3 | 0.58 | 0.8 | 0.4 |
| | 0.016 × 0.022 | 70.0 | Large | Large | 0.9 | 0.65 | 0.3 | 0.0 |
| | 0.016 × 0.025 | 70.0 | Large | Large | 1.1 | 0.47 | 0.4 | 0.2 |
| | 0.017 × 0.025 | 70.0 | Large | Large | 0.9 | 0.50 | 0.2 | 0.0 |
| | 0.018 × 0.025 | 70.0 | Large | Large | 0.9 | 0.24 | 0.3 | 0.1 |
| | 0.019 × 0.025 | 70.0 | Large | Large | 1.4 | 0.39 | 0.5 | 0.4 |
| | | | | Avg = | 1.1 | 0.42 | Avg = 0.4 | 0.2 |

These results demonstrate that predictable frictional engagement between an orthodontic stop and an archwire can be achieved by using the disclosed methods to define a non-linear path through an orthodontic stop. The non-linear path creates points of contact inside the stop that bend the archwire as it passes through the stop. The difference in frictional engagement with the posterior and anterior portions of the archwire prove that the formed stops are non-linear and that the non-linearity interacts with the curvature of the archwire to produce significant and advantageous variation in the frictional engagement between the stop and the archwire. The results show that consistently useful results are achievable using real world components and methods. Unexpectedly, all common wire sizes and shapes can be accommodated with just two stop sizes and only two die sets, one for each size stop.

As shown in FIG. 12, the above discussed experiments were conducted with the archwire positioned so that any non-linearity defined by the stop occurs is in the same plane as the curvature of the archwire. With the non-linear path through the stop in the same plane as the curvature of the archwire, the frictional engagement between the stop and the archwire will vary according to the difference between the curvature of the archwire and the curvature of the bend moment imposed within the stop.

Aligning the curvature of the bend imposed by the stop results in variable frictional engagement, but such a relationship between the non-linearity defined by the stop and the curvature of the archwire is not mandatory. A stop defining a non-linear path for the archwire will also produce useful and repeatable frictional engagement with the archwire when the non-linearity defined by the stop is perpendicular to the plane containing the curvature of the archwire. Such a stop would have the same frictional engagement with the archwire along the entire length of an archwire whose curvature is in a flat plane. The frictional engagement would be selected to prevent the stop from falling off the archwire during packaging, transport and clinical use, while also permitting easy adjustment during patient care. By varying the configuration of the non-linear path, the resulting bend imposed on the archwire, and other variables, a suitable frictional engagement can be created according to the disclosed methods.

It is anticipated that the disclosed non-linear stops can be used directly when field threading of tubes is indicated. Appropriate tube sizes will be required for the wire size that is used. It is also anticipated that pre-threaded tubes on wires will be sold as an assembly. Assemblies of tubes on wires can be generated by a number of processes including by hand as well as by numerous semi- or fully automated processes.

What is claimed:

1. A method of making an archwire assembly comprising:
   assembling a tubular crimpable stop onto an archwire having a curve in at least a first plane;
   forming said crimpable stop to define a non-linear path through said stop while said crimpable stop is on said archwire;
   wherein said non-linear path imposes a bending moment between the archwire and crimpable stop within the crimpable stop, generating a frictional engagement between said crimpable stop and said archwire, said frictional engagement sufficient to maintain the crimpable stop on said archwire but permitting said crimpable stop to be repositioned along said archwire, wherein said step of forming further comprises: placing said archwire and crimpable stop between a pair of dies with said archwire positioned so that movement of one die relative to the other die occurs in a direction aligned with said first plane, said dies configured to deform said crimpable stop into a non-linear configuration; and bringing the two dies together on the crimpable stop and archwire, thereby deforming said crimpable stop into said non-linear configuration.

2. The method of making an archwire assembly of claim 1, wherein said archwire curve is defined by different radii of curvature, resulting in a curvature that varies along a length of said archwire between first and second free ends of the archwire, said curvature varying from a first radius of curvature adjacent the free ends of the archwire to a second radius of curvature at a point intermediate said free ends, said second radius of curvature being smaller than said first radius of curvature; and wherein
   said step of assembling further comprises placing a tubular crimpable stop onto said archwire, said tubular crimpable stop having a substantially linear central axis generally aligned with a length of said archwire; and
   said step of forming further comprises applying pressure to said straight tubular crimpable stop sufficient to deform said straight tubular crimpable stop into a curved configuration defining a central axis having a radius of curvature less than said first radius of curvature.

3. The method of making an archwire assembly of claim 2 wherein said pressure applied to said straight tubular crimpable stop is insufficient to plastically deform said archwire.

4. A method of using an orthodontic stop on an orthodontic archwire assembly comprising:
   selecting an archwire including more than one radius of curvature;
   pre-assembling at least one crimpable stop that defines a non-linear path through the stop onto an archwire to form an archwire assembly wherein said non-linear path imposes a bending moment between the archwire and crimpable stop within the crimpable stop, generating a frictional engagement between said crimpable stop and said archwire, said frictional engagement sufficient to maintain the crimpable stop on said archwire but permitting said crimpable stop to be repositioned along said archwire, the frictional engagement between the crimpable stop and archwire varies according to the radius of curvature of the archwire, the frictional engagement between the crimpable stop and the archwire increasing with the radius of curvature of the archwire; and
   finally assembling said archwire assembly by repositioning said crimpable stop to a desired location on said archwire, and crimping said crimpable stop to fix said stop to said archwire in said desired location.

5. The method of using an orthodontic stop on an orthodontic archwire of claim 4, wherein said orthodontic archwire has a curvature in at least a first plane, and said step of pre-assembly further comprises:
   selecting a tubular crimpable stop having a non-linear path configured so that said archwire contacts said stop at a plurality of longitudinally spaced points along an inside surface of said tubular stop, two of said points being on an outside of said curvature and at least one of said points being on an inside of said curvature and intermediate said two of said points.

6. The method of using an orthodontic stop on an orthodontic archwire of claim 4, wherein said archwire has a variable curvature defined by a plurality of radii of curvature from a maximum radius of curvature to a minimum radius of curvature and said step of pre-assembly further comprises:
   selecting said crimpable stop so that said non-linear path imparts a bend on said archwire, said bend having a radius of curvature smaller than said maximum radius of curvature.

7. The method of making an archwire assembly of claim 1, wherein said step of forming results in an inside surface of said crimpable stop including three points of contact with said archwire, two of said points of contact being longitudinally spaced along said archwire and one point of contact being intermediate said two of said points of contact.

8. The method of making an archwire assembly of claim 7 comprising selecting an archwire having an anterior portion at least in part defined by a first radius of curvature and a pair of posterior legs defined at least in part by a second radius of curvature larger than the first radius of curvature, wherein said bending moment has a third radius of curvature smaller than said second radius of curvature, resulting in frictional engagement between said crimpable stop and said archwire sufficient to prevent said crimpable stop from moving on said posterior legs when exposed to a force equal to the weight of the crimpable stop.

9. A method of making an archwire assembly comprising:
   assembling a tubular crimpable stop onto an archwire having a curve in at least a first plane;
   forming said crimpable stop to define a non-linear path through said stop while said crimpable stop is on said archwire, said non-linear path including an inside surface of said crimpable stop having three points of contact with said archwire, two of said points of contact being longitudinally spaced along said archwire and one point of contact being intermediate said two of said points of contact;
   wherein said non-linear path imposes a bending moment between the archwire and crimpable stop within the crimpable stop, generating a frictional engagement between said crimpable stop and said archwire, said frictional engagement sufficient to maintain the crimpable stop on said archwire but permitting said crimpable stop to be repositioned along said archwire.

10. The method of making an archwire assembly of claim 9 comprising selecting an archwire having an anterior portion at least in part defined by a first radius of curvature and a pair of posterior legs defined at least in part by a second radius of curvature larger than the first radius of curvature, wherein said bending moment has a third radius of curvature smaller than said second radius of curvature, resulting in frictional engagement between said crimpable stop and said archwire sufficient to prevent said crimpable stop from moving on said posterior legs when exposed to a force equal to the weight of the crimpable stop.

\* \* \* \* \*